(12) United States Patent
Gardiner et al.

(10) Patent No.: US 11,224,676 B2
(45) Date of Patent: Jan. 18, 2022

(54) FOAM IN WOUND TREATMENT

(71) Applicant: Mölnlycke Health Care AB, Gothenburg (SE)

(72) Inventors: Eric S. Gardiner, Granville, NY (US); Jason Raymond Johnson, Rockland, ME (US)

(73) Assignee: Mölnlycke Health Care AB, Gothenburg (SE)

( * ) Notice: Subject to any disclaimer, the term of this patent is extended or adjusted under 35 U.S.C. 154(b) by 0 days.

(21) Appl. No.: 16/607,435

(22) PCT Filed: Jun. 5, 2018

(86) PCT No.: PCT/EP2018/064769
§ 371 (c)(1),
(2) Date: Oct. 23, 2019

(87) PCT Pub. No.: WO2018/224499
PCT Pub. Date: Dec. 13, 2018

(65) Prior Publication Data
US 2020/0129655 A1   Apr. 30, 2020

(30) Foreign Application Priority Data
Jun. 9, 2017 (EP) .................................... 17175238

(51) Int. Cl.
| | |
|---|---|
| *A61L 15/26* | (2006.01) |
| *A61L 15/18* | (2006.01) |
| *A61L 15/42* | (2006.01) |
| *A61L 15/48* | (2006.01) |
| *A61L 15/60* | (2006.01) |
| *C08G 18/10* | (2006.01) |
| *C08G 18/76* | (2006.01) |
| *C08J 9/00* | (2006.01) |
| *C08J 9/28* | (2006.01) |

(52) U.S. Cl.
CPC .............. *A61L 15/26* (2013.01); *A61L 15/18* (2013.01); *A61L 15/425* (2013.01); *A61L 15/48* (2013.01); *A61L 15/60* (2013.01); *C08G 18/10* (2013.01); *C08G 18/7621* (2013.01); *C08J 9/0066* (2013.01); *C08J 9/28* (2013.01); *C08G 2110/005* (2021.01); *C08J 2201/04* (2013.01); *C08J 2205/044* (2013.01); *C08J 2375/04* (2013.01)

(58) Field of Classification Search
None
See application file for complete search history.

(56) References Cited

U.S. PATENT DOCUMENTS

| | | | |
|---|---|---|---|
| 4,230,822 A | 10/1980 | Murch et al. | |
| 2002/0062097 A1 | 5/2002 | Simpson | |
| 2014/0180187 A1* | 6/2014 | Croizat | ................... A61L 15/20 602/45 |

FOREIGN PATENT DOCUMENTS

| | | |
|---|---|---|
| WO | WO 00/020281 A1 | 4/2000 |
| WO | WO 2007/149418 A2 | 12/2007 |
| WO | WO 2008/101652 A1 | 8/2008 |
| WO | WO2016169752 A1 * | 10/2016 |
| WO | PCT/EP2018/064769 | 6/2018 |

OTHER PUBLICATIONS

"Alumina Trihydrate Info" (accessed from http://cameo.mfa.org/wiki/Alumina_trihydrate).*
"International Standard ISO 13322", International Organization for Standarization, 2014.*
Kang et al., "Effect of Nucleating Agents on the Morphological, Mechanical and Thermal Insulating Properties of Rigid Polyurethane Foams", 2009, Macromolecular Research, vol. 17, No. 11, pp. 856-862.*
"T558 Official Method", Technical Association of the Pulp and Paper Industry, 1997.*
International Search Report and Written Opinion were dated Aug. 6, 2018 by the International Searching Authority for International Application No. PCT/EP2018/064769, filed on Jun. 5, 2018 and published as WO 2018/224499 on Dec. 13, 2018(Applicant—Mölnlycke Health Care AB) (9 Pages).

\* cited by examiner

*Primary Examiner* — Robert A Wax
*Assistant Examiner* — Randeep Singh
(74) *Attorney, Agent, or Firm* — Ballard Spahr LLP

(57) ABSTRACT

The present invention relates to a hydrophilic foam material, which is of particular use in wound treatment, and to a method for producing said hydrophilic foam material. The hydrophilic foam material has nucleating particles, wherein at least 85% of all foam cells in said material have an average cell size of 0.01 mm$^2$ or less.

11 Claims, 3 Drawing Sheets

FOAM IN WOUND TREATMENT

CROSS-REFERENCE TO RELATED APPLICATIONS

This application is a U.S. National Phase Application of International Application No. PCT/EP2018/064769, filed Jun. 5, 2018, which claims priority to European Application No. 17175238.9, filed Jun. 9, 2017, each of which are hereby incorporated by reference in their entirety.

FIELD OF THE INVENTION

The present invention relates to a hydrophilic foam material, which is of particular use in wound treatment, and to a method for producing said hydrophilic material.

BACKGROUND OF THE INVENTION

Wound dressings are used to heal and protect wounds. The capability of the wound dressing to absorb and retain exudate from the wound is of paramount importance for the healing process. The liquid handling capacity of a dressing affects the frequency of dressing changes, which should be minimized to promote wound healing. In various applications, hydrophilic materials are used in wound dressings to absorb and retain wound fluids, further particularly hydrophilic foams such as hydrophilic open-cell polyurethane foams.

It is therefore paramount that a hydrophilic foam material, when used in a wound dressing, in particular in a wound dressing for treatment of high exuding wounds, has desirable liquid handling capabilities including foam properties such as liquid absorbency speed and capacity, liquid retention capacity, and liquid transfer and spreading capacity.

Hence, there is a need in the art to provide a hydrophilic foam material with improved fluid handling capacity, in particular for use as or in a medical dressing, wherein at least one of the above discussed foam properties is optimized.

SUMMARY OF THE INVENTION

According to a first aspect of the invention, these and other objects are achieved through a hydrophilic polyurethane foam material comprising nucleating particles present at a concentration of at least 5% by weight, relative to the overall weight of the foam material, wherein at least 85% of all foam cells in said foam material have an average cell size of 0.01 mm$^2$ or less, as measured by image analysis based on ISO 13322-1:2014.

In standard foam manufacturing processes it is often difficult to control the foam cell size, thus resulting in a foam material with a relatively wide range of different cell sizes. As the foam cell size is critical for various physical properties of the foam material, it would be highly desirable to better control the foam cell size to thereby ensure that a desirable property, and associated functionality, is consistently achieved across the entire volume of the foam material.

For example, in case a layer of the foam material is used as or in a medical dressing, it is desirable that the foam layer has a substantially homogenous foam cell size across the foam layer, thereby ensuring that a given desirable property (e.g. absorption capacity) is achieved across the foam layer.

The inventors have realized that a hydrophilic polyurethane foam material with improved homogeneity in terms of foam cell size can be achieved by means of including nucleating particles into the foam, already at the stage of foam manufacturing.

In particular, the inventors have realized that reducing the foam cell size improves the fluid absorption per volume of foam, as well as speed of absorption of the foam. In addition, by means of providing a hydrophilic foam with a substantially homogenous cell size, liquid spreading within the foam can be improved.

In accordance with the present invention, the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups.

Preferably, the term "hydrophilic" refers to the water-permeability property of a material or the water-attracting property of a molecule. In the context of a material with pores (such as, for example, open-cell foams) or materials with through-holes, such a material is "hydrophilic" if the material takes up water.

In accordance with the present invention the "average cell size" is to be understood as the (largest) cross-sectional area of the cell, wherein a spherical approximation of the cell is applied. The cell diameter is measured by image analysis of a cross-section of the foam material, wherein the image analysis method is based on ISO 13322-1:2014, and cross-sectional area of the cell is calculated accordingly.

In embodiments of the invention, the foam material comprises interconnected foam cells, which preferably result in a substantially open-cell structure.

As used herein, the term "open-cell" refers to the pore (or cell) structure of the foam, wherein the pores in a pore structure are connected to each other and form an interconnected network with pathways for fluid flow through the foam material, such foam pore structure is commonly referred to as "reticulated foam". "Substantially" open-cell structures have at least 95%, preferably at least 99% of pores that are connected with at least one other pore.

In embodiments of the invention, the nucleating particles are present at a concentration of from 5 to 25%, preferably from 5 to 20%, by weight, relative to the overall weight of said foam material.

The inventors have realized that the nucleating particles should be present at a concentration of at least 5% (w/w) in order to substantially increase the number of nucleation sites in the foaming process, and thus provide improved control of the average cell size in the resulting foam.

The inventors have further realized that the concentration of nucleating particles should advantageously be less than 25% w/w, as higher concentrations of nucleating particles may result in increased stiffness of the foam material (i.e. a less flexible) and/or dusting of nucleating particles (i.e. at higher concentration of nucleating particles, the risk exists that some nucleating particles are not substantially encapsulated in the foam material). Both of said potential effects (i.e. increased stiffness and dusting) are typically not desirable, in particular in case the foam material is used as or in a medical dressing.

In embodiments of the invention, the nucleating particles have a particle size in the range of from 1 to 30 μm, preferably from 1 to 20 μm, and more preferably from 1 to 10 μm. The particles are preferably essentially spherical in shape.

It should be understood the nucleating particles typically have a defined particle size distribution. In accordance with the present invention, the term "particle size" refers to the median particle size of said particle size distribution (i.e. the "D50-value").

The inventors have further realized that the particles size of the nucleating particles may advantageously be less than 30 μm, preferably less than 20 μm, or less than 15 μm, or less than 10 μm. This is advantageous, because larger particle sizes, i.e. above 30 μm, may result in larger foam cells in the foaming process, for example due to the formation of several adjacent foam cells (on the surface of a single nucleating particle) which subsequently collapse into one (or less) cells. As discussed above, a smaller foam cell size is believed, without wishing to be bound by theory, to provide for a more flexible foam with a higher absorption capacity per volume unit, as compared with a corresponding foam material with larger foam cell size.

Furthermore, comparatively smaller particles sizes provide for a higher surface area per weight unit of the nucleating particles, thereby providing more nucleation sites per weight unit of the nucleating particles.

In embodiments of the invention, the surface area of the nucleating particles is more than 1 $m^2/g$, preferably more than 2 $m^2/g$, more preferably more than 5 $m^2/g$, as measured according to ISO 9277:2010 (BET method).

In embodiments of the invention, the nucleating particles comprise or essentially consist of particles that are selected from the group consisting of alumina trihydrate, calcium carbonate, carbon black, magnesium oxide, lime, clay, and diatomaceous earth.

In embodiments of the invention, the nucleating particles comprise, preferably essentially consist of, alumina trihydrate (chemical structure $Al_2O_3 \cdot 3H_2O$ or $2\,Al(OH)_3$).

In embodiments of the invention, the nucleating particles are substantially encapsulated within said foam material. Thereby, release of the nucleating particles from the foam material is avoided or at least minimized. This is particularly advantageous in case the hydrophilic foam material is used as, or in a medical dressing.

Preferably, at least 95% of all particles, further preferably at least 99% of all particles are encapsulated within said foam material.

In embodiments of the invention, the foam material further comprises a surfactant present at a concentration of from 0.05 to 0.5% by weight, relative to the overall weight of the foam material.

In embodiments of the invention, the foam material is characterized by a free swell absorptive capacity, corresponding to the maximum absorptive capacity, of at least 800 $kg/m^3$, preferably at least 900 $kg/m^3$, more preferably at least 1000 $kg/m^3$.

In embodiments of the invention, the foam material is characterized by a free swell absorptive capacity, corresponding to the maximum absorptive capacity, of from 800 to 2500 $kg/m^3$ as measured by EN 13726-1:2002.

In embodiments of the invention, the foam material has a speed of absorption of at least 5 μL/sec, preferably at least 10 μL/sec, more preferably at least 20 μL/sec.

In embodiments of the invention, the speed of absorption of the foam material, according to embodiments of the invention, is at least 25% greater, preferably at least 50% greater, than the corresponding foam material without said nucleating particles.

In accordance with the invention, the term "speed of absorption" is defined as the speed of absorbing a given volume of a fluid (volume/ time) as measured according to TAPPI standard T558 OM-97 using 30 μL of Solution A according to EN 13726-1:2002, as test solution.

Solution A, as defined in EN 13726-1, consists of a sodium chloride and calcium chloride solution containing 142 mmol of sodium ions and 2.5 mmol of calcium ions as the chloride salts. This solution has an ionic composition comparable to human serum or wound exudate. Said solution is prepared by dissolving 8.298 g of sodium chloride and 0.368 g of calcium chloride dihydrate in deionized water up to the "1 L" marking in a volumetric flask.

In embodiments of the invention, the hydrophilic foam material does not comprise any particles or structural units other than the nucleating particles according to the present invention, in particular no filler or reinforcement agent.

In embodiments of the invention, the hydrophilic foam material is an open-cell porous hydrophilic foam having a density of 60 to 180 $kg/m^3$, preferably 80 to 130 $kg/m^3$, more preferably 90 to 120 $kg/m^3$, as measured according to standard method ISO 845:2006.

In embodiment of the invention the hydrophilic foam material is realized as a layer.

A "layer" as used in accordance with the present invention should generally be understood to have a continuous extension in one plane (x and y direction) and a thickness perpendicular to said plane (z direction).

In embodiments of the invention, the foam layer has a thickness of from 0.5 mm to 30 mm, preferably from 1 mm to 10 mm, more preferably from 1 to 7 mm, such as from 1 mm to 5 mm.

In embodiments of the invention, the hydrophilic foam material, preferably the foam layer comprise(s) an antimicrobial agent.

In embodiments of the invention, the antimicrobial particle comprises silver. In embodiments of the invention, the silver is metallic silver. In embodiments of the invention, the silver is a silver salt.

In embodiments of the invention, the silver salt is silver sulfate, silver chloride, silver nitrate, silver sulfadiazine, silver carbonate, silver phosphate, silver lactate, silver bromide, silver acetate, silver citrate, silver carboxymethyl cellulose (CMC), silver oxide. In embodiments of the invention, the silver salt is silver sulfate.

In embodiments of the invention, the antimicrobial particle comprises a monoguanide or biguanide. In embodiments of the invention, the monoguanide or biguanide is chlorhexidine digluconate, chlorhexidine diacetate, chlorhexidine dihydrochloride, polyhexamethylene biguanide (PHMB) or a salt thereof, or polyhexamethylene monoguanide (PHMG) or a salt thereof. In embodiments of the invention, the biguanide is PHMB or a salt thereof.

In embodiments of the invention, the antimicrobial particle comprises a quaternary ammonium compound. In embodiments of the invention, the quaternary ammonium compound is cetylpyridinium chloride, benzethonium chloride, or poly-DADMAC. In embodiments of the invention, the antimicrobial particle comprises triclosan, sodium hypochlorite, copper, hydrogen peroxide, xylitol, or honey.

According to a second aspect of the invention, the above-mentioned and other objects are achieved by means of providing a medical dressing (in particular a wound dressing) comprising a layer of the hydrophilic polyurethane foam material according to the invention.

In embodiments of the invention, the medical dressing further comprises at least one further layer (further to the layer of hydrophilic polyurethane foam material), preferably a backing and/or an adhesive layer or coating, preferably two or more of these further layers.

The term "medical dressing" should be understood as a dressing that is suitable to use in treatment of wounds, i.e. a "wound dressing", and/or a dressing that can be used to prevent wounds or injuries to occur, e.g. to prevent pressure ulcer.

In accordance with the present invention, the term "wound site" or "wound" is to be understood as any open or closed wound, for example, including inter alia (but not limited to) chronic wounds, acute wounds, and post-operative wounds such as e.g. closed incisions and scar treatment.

The embodiments, features and effects described above in connection with the hydrophilic polyurethane foam material according to the first aspect of the invention are applicable, mutatis mutandis, for the above described medical dressing according to the second aspect of the invention.

According to a third aspect of the invention, the above-discussed and other objects are achieved through a method of making a hydrophilic polyurethane foam material, said method comprising the steps of:

(i) preparing an aqueous mixture,
(ii) mixing said aqueous mixture with a prepolymer composition, and
(iii) allowing the resulting emulsion (of step (ii)) to cure wherein nucleating particles, at a concentration of at least 5% by weight of said prepolymer composition, are added to said aqueous mixture in step (i) and/or are present in said prepolymer composition of step (ii), preferably wherein said aqueous mixture of step (i) comprises a surfactant.

In embodiments of the invention, the hydrophilic polyurethane foam material as used in all embodiments of the present invention described above may be obtained from a prepolymer comprising or being an isocyanate-capped polyol or isocyanate-capped polyurethane.

In accordance with the present invention, the term "prepolymer" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a polymer or oligomer the molecules of which are capable of entering, through reactive groups, into further polymerization and thereby contributing more than one structural unit to at least one type of chain of the final polymer.

In embodiments of the invention, the prepolymer derives from a reaction between a polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the polyol is selected from the group consisting of polyester polyols, polyacrylate polyols, polyurethane polyols, polycarbonate polyols, polyether polyols, polyester-polyacrylate polyols, polyurethane polyacrylate polyols, polyurethane polyester polyols, polyurethane polyether polyols, polyurethane polycarbonate polyols and polyester polycarbonate polyols, among others, in particular polycondensates of di or optionally tri-, and tetrols as well as di or optionally tri- and tetracarboxylic acids or hydroxycarboxylic acids or lactones.

Exemplary suitable diols are ethylene glycol, butylene glycol, diethylene glycol, triethylene glycol, polyalkylene glycols such as polyethylene glycol, and also 1,2-propanediol, 1, 3-propanediol, 1,3-butanediol, 1,4-butanediol, 1,6-hexanediol and isomers, neopentyl glycol or neopentyl glycol hydroxypivalate. In addition, polyols such as trimethylolpropane, glycerol, erythritol, pentaerythritol, trimethylolbenzene or trishydroxyethyl isocyanurate are also within the scope of the present invention.

In embodiments of the invention, the prepolymer derives from a reaction between a polyol and a diisocyanate compound that is aliphatic. For example, in embodiments of the invention, the diisocyanate compound is or comprises hexamethylene diisocyanate (HDI). Accordingly, in embodiments of the invention, the prepolymer is or comprises an hexamethylene isocyanate-capped polyol or hexamethylene isocyanate-capped polyurethane.

In embodiments of the invention, the prepolymer is or comprises a hexamethylene isocyanate-capped polyethylene glycol.

In embodiments of the invention, the prepolymer derives from a reaction between said polyol and a diisocyanate compound that is aromatic. For example, in embodiments of the invention, the diisocyanate compound is or comprises toluene diisocyanate (TDI), methylene diphenyl diisocyanate (MDI). Accordingly, in embodiments of the invention, the prepolymer is or comprises a toluene isocyanate-capped polyol or a methylene diphenyl isocyanate-capped polyol or toluene isocyanate-capped polyurethane or methylene diphenyl isocyanate-capped polyurethane.

In embodiments of the invention, the prepolymer is or comprises a toluene isocyanate-capped polyethylene glycol. In embodiments of the invention, the prepolymer is or comprises a methylene diphenyl isocyanate-capped polyethylene glycol.

According to a fourth aspect of the invention, the above-discussed and other objects are achieved through the use of nucleating particles for producing a hydrophilic polyurethane foam material, wherein at least 85% of all foam cells in said foam material have an average cell size of 0.01 mm$^2$ or less, as measured by image analysis based on ISO 13322-1:2014

In the claims, the terms "comprising" and "comprise(s)" do not exclude other elements or steps, and the indefinite article "a" or "an" does not exclude a plurality of elements or steps. For example, the hydrophilic polyurethane foam material, which may be obtained from a prepolymer as disclosed above, may be also be obtained from a mixture of a plurality of different prepolymers, in particular another polyurethane polymer and/or another (additional) polymer that is not a polyurethane polymer.

The mere fact that certain measures are recited in mutually different dependent claims does not indicate that a combination of these measured cannot be used to advantage.

BRIEF DESCRIPTION OF THE DRAWINGS

These and other aspects of the invention will now be shown in more detail, with reference to the Figures showing exemplary embodiments of the invention, wherein.

DESCRIPTION OF EMBODIMENTS OF THE INVENTION

In the following, detailed embodiments of the present invention are described, with reference to the accompanying Figures, which are exemplary illustrations of embodiments of the invention.

Figure 1:
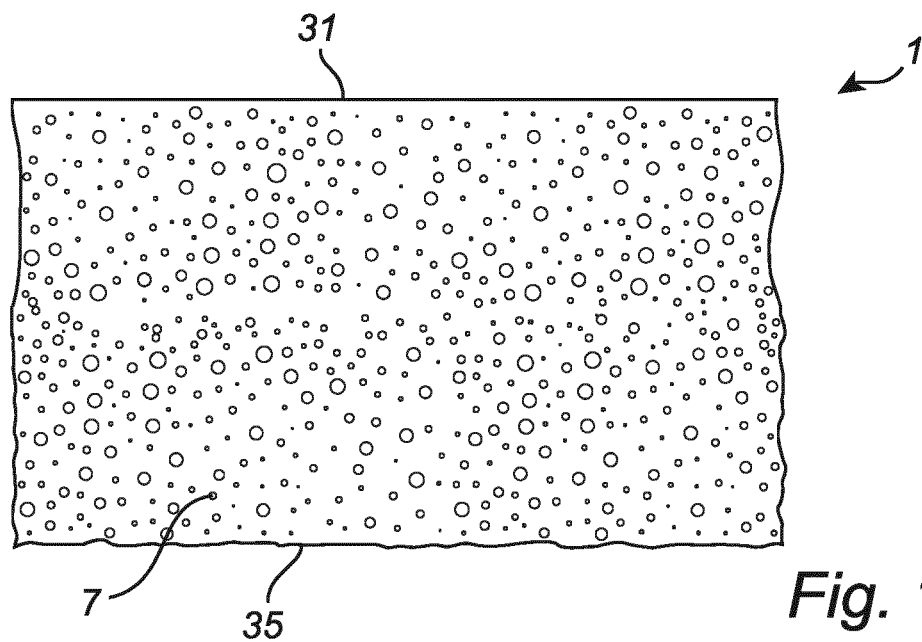
FIG. 1 is a cross-sectional view of an embodiment of a layer of a hydrophilic polyurethane foam material according to the invention.

FIG. 1 illustrates a foam layer 1 comprising a hydrophilic polyurethane foam material 7 according to an embodiment of the invention.

The foam layer has a top side 31 and bottom side 35, opposite to the top side 31.

The hydrophilic polyurethane foam material 7 in accordance with the present invention comprises nucleating particles at a concentration of at least 5% by weight of the foam material (relative to the overall weight of the foam), wherein at least 85% of all foam cells in said foam material has an average cell size of 0.01 mm$^2$ or less, as measured by image analysis based on ISO 13322-1:2014.

Accordingly, a hydrophilic polyurethane foam material 7 is provided with substantially homogenous small cell sizes (at least 85% of all foam cells have an average cell size of 0.01 mm$^2$ or less), thereby improving at least one of the following foam properties associated with the liquid handling capacity of the foam material 7: liquid absorption (speed and maximum), and liquid spreading and transport within the foam material 7.

FIGS. 2a-d illustrate exemplary embodiments of medical dressings 20, 50, 80, 90 comprising the hydrophilic polyurethane foam material 7, as realized in the form of a layer 1. In embodiments of the invention, as shown in FIGS. 2a-d, the medical dressings 20, 50, 80, 90 further comprise a backing layer 21, 23 overlaying the top side 31 of the foam layer 1, wherein bottom side 35 is adapted to function as the skin or wound facing side which can thus function as a direct or indirect wound contact side through which side wound exudate can be absorbed and transported into the core of the foam layer 1.

The inventors have surprisingly realized that if the cell size of a hydrophilic polyurethane foam material is reduced, the speed of absorption of liquid (e.g. wound exudate) is increased. For example, in embodiments of the invention, the foam layer 1 according to the present invention has a speed of absorption of at least 10 μL/sec, preferably at least 20 μL/sec, more preferably at least 30 μL/sec.

Figure 2A:
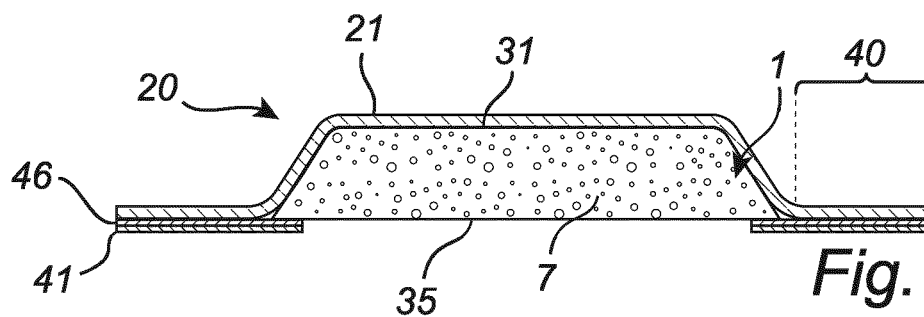
FIGS. 2a-d are cross-sectional views of embodiments of a medical dressing according to the invention.
Figure 2B:
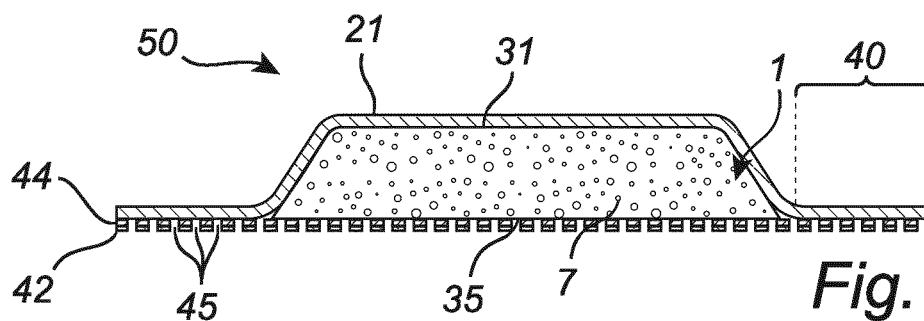

In embodiments of the invention, as shown in FIGS. 2a-b, the backing layer 21 extends outside the peripheral portion of the foam layer 1, to define a border portion 40 of the backing layer 21 thus surrounding the peripheral portion the foam layer 1, thereby providing a so-called island dressing.

Suitable backing layers 21, 23 are, for example, films, foils, foams, or membranes. Furthermore, it is advantageous if the backing layer has a thickness in the area of from ≥5 μm up to ≤80 μm, particularly preferred of from ≥5 μm up to ≤60 μm, and particularly preferred of from ≥10 μm up to ≤30 μm and/or that the backing layer has an elongation at break of more than 450%.

The backing layer 21, 23 may be realized to be pervious to water vapor in accordance to DIN 53333 or DIN 54101.

Preferably, the backing layer 21, 23 may comprise a thermoplastic polymer, for example as a coating, or may consist thereof. A thermoplastic polymer, at first, is to be understood as a polymer that remains thermoplastic if the same is repeatedly heated and cooled within a temperature that is typical for the respective processing or application conditions. Being thermoplastic is understood to be the property of a polymer material to repeatedly soften upon application of heat and to repeatedly harden when cooled down, within a temperature range that is typical for the respective material, wherein the material remains capable of being formed, in the softened stage, and repeatedly, by way of flowing, for example as a shaped article, extruded or otherwise.

Preferred thermoplastic polymers are polyurethane, polyethylene, polypropylene, polyvinyl chloride, polystyrene, polyether, polyester, polyamide, polycarbonate, polyether polyamide copolymers, polyacrylate, polymethacrylate, and/or polymaleate. Preferably, the thermoplastic polymers are elastomeric. It is particularly preferred that the carrier foil comprises thermoplastic polyurethanes (TPU), or consists thereof. Thermoplastic polyurethanes selected from the group comprising aliphatic polyester polyurethanes, aromatic polyester polyurethanes, aliphatic polyether polyurethanes and/or aromatic polyether polyurethanes are particularly suitable. By using these polymers, it is possible to obtain backing layers as breathable elastic membrane films. These are characterized by high flexibility and elasticity over a broad range of temperatures, also having advantageous sealing properties for (liquid) water while having a high water vapor permeability. These materials are further characterized by low noise, advantageous textile feel, resistance against washing and cleaning, very good chemical and mechanical resistance and the fact they are free of plasticizers.

Particular preferred is also a backing layer that acts as a barrier for germs and has a high sealing capability against exudate emanating from the wound while, at the same time, being permeable for water vapor. In order to achieve the same, the backing layer may, for example, be realized as a semipermeable membrane.

In embodiments of the invention, the backing layer 21, 23 is preferably vapor permeable. The backing layer 21, 23 may be a plastic film, for example, comprising or consisting of polyurethane, polyethylene, or polypropylene. In embodiments of the invention, the backing layer 21, 23 is a polyurethane film having a thickness in the range of 10 to 100 μm, for example, 10 to 80 μm such as 10 to 50 μm, preferably from 10 μm to 30 μm.

As schematically illustrated in FIGS. 2a-d, the medical dressings 20, 50, 80, 90 may include an adhesive layer or coating 41, 42, 43 to adhere the medical dressing to a wound site (wound surface and/or the surrounding skin surface). In embodiments of the invention, the adhesive layer or coating 41, 42, 43 may be a silicone based adhesive or an acrylic based adhesive, preferably the adhesive layer or coating is a silicone based adhesive. The term "coating" should, in accordance with the present invention, be understood as essentially one continuous layer on a surface, or a discontinuous cover on a surface.

The medical dressings 20, 50, 80, 90 may furthermore comprise a release layer (not shown) that is releasably connected to the adhesive layer or coating 41, 42, 43 and can be removed prior to application. Suitable release layers comprise or consist of materials that have limited adhesion to the adhesive of the adhesive layer, if brought in contact with the same. Examples for such release layers are release papers that comprise a non-adhesive silicone or polyolefin layer.

Figure 2C:
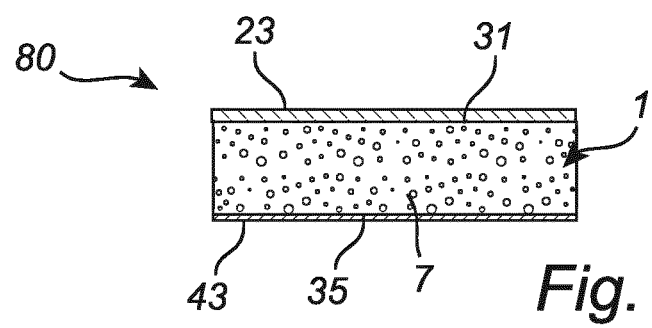
Figure 2D:
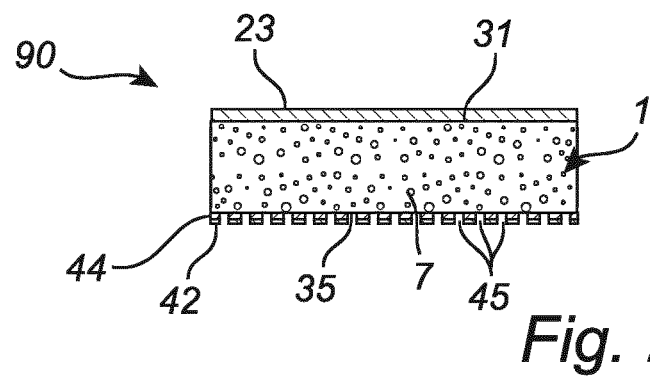

As shown in FIG. 2b and FIG. 2d, the medical dressings 50, 90 preferably include a perforated layer 44, for example made of a polyurethane film, wherein an adhesive layer or coating 42 is provided on the non-perforated portions of the perforated layer 44. The perforated layer 44 includes a plurality of openings 45 (or through holes) of any desirable size and shape. The shape and size of the openings 45 may be adapted to achieve a desirable liquid transport from the wound to the above first foam layer 1.

In embodiments of the invention, as illustrated in FIG. 2*b*, the perforated layer 44 with the adhesive layer or coating 42 may be provided on the bottom side 35 of the foam layer 1, wherein the perforated layer 44 extends outside the peripheral portion of the foam layer 1 and is attached (e.g. by means of a second adhesive, not shown) to the border portion 40 of the backing layer 21.

In alternative embodiments, as shown in FIG. 2*d*, the extension in x-y direction of the perforated layer 44 corresponds to the extension in x-y direction of the foam layer 1. In embodiments of the invention, as shown in FIG. 2*c* the adhesive layer or coating 43 is provided directly on the bottom side 35 of the foam layer 1. In embodiments of the invention, as shown in FIG. 2*a*, an adhesive layer or coating 41 is provided on a continuous plastic film 46, for example a polyurethane film as discussed above, which continuous plastic film 46 is arranged adjacent to a peripheral portion of the foam layer 1, wherein the continuous film 46 extends away from said peripheral portion and is attached (e.g. by means of a second adhesive, not shown) to the border portion 40 of the backing layer 21. In further embodiments (not shown) an adhesive layer or coating may be provided directly on a skin facing surface of the border portion 40 of the backing layer 21.

The person skilled in the art realizes that the present invention by no means is limited to the exemplary embodiments described herein. For example, the medical dressing according to invention may comprise additional structural layer(s) in fluid communication with the hydrophilic polyurethane foam material to further optimize desirable properties and/or to achieve additional functionalities. For example, the medical dressing may comprise a second hydrophilic foam layer and/or a non-woven layer with absorption capacity, to thereby further optimize the liquid handling capacity of the medical dressing.

The invention is further illustrated in the following Examples. Unless otherwise specified, all experiments and tests described herein were performed at standard laboratory conditions, in particular at room temperature (20° C.) and standard pressure (1 atm.). Unless indicated otherwise, all indications regarding percentages are meant to refer to percentage by weight.

EXAMPLE 1

Method of Preparing a Hydrophilic Polyurethane Foam

A foam layer was prepared using the following steps (1)-(3): (1) An aqueous mixture comprising surfactant Pluronic® L62 0.125% w/w was prepared; (2) the aqueous mixture was mixed with the prepolymer Trepol® B1, at a 1.6:1 ratio by weight (aqueous mix./prepolymer) to give an emulsion mixture; (3) the emulsion mixture was poured onto and spread out on a casting paper (20×30 cm) and was allowed to cure at standard condition (at room temperature) to give a foam with a thickness of about 3 mm (foam thickness is controlled by adapting the thickness of spread of the emulsion mixture in step (3)). Chemicals used are commercially available and are, in particular: Trepol® B1 (TDI based prepolymer) from Rynel Inc., and Pluronic® L62, commercially available from BASF.

EXAMPLE 2

Method of Preparing a Hydrophilic Polyurethane Foam with Added Nucleating Particles A foam layer was prepared using the following steps (1)-(3): (1) An aqueous mixture comprising surfactant Pluronic® L62 0.125% w/w and alumina trihydrate 7% w/w (SB-432 commercially available from Akrochem Corporation; 7% w/w of aqueous mix. corresponds to ca. 10% w/w of the final dried foam product, given prepolymer mixture ratio in step (2)) was prepared; (2) the aqueous mixture was mixed with the prepolymer Trepol® B1 at 1.6:1 ratio by weight (Aqueous mix./prepolymer) to give an emulsion mixture; (3) the emulsion mixture was poured onto and spread out on a casting paper (20×30 cm) and was allowed to cure at standard condition (at room temperature) to give a foam having a thickness of about 3 mm (foam thickness is controlled by adapting the thickness of spread of the emulsion mixture in step (3)).

EXAMPLE 3

Foam Pore Cell Size Analysis

Figure 3:
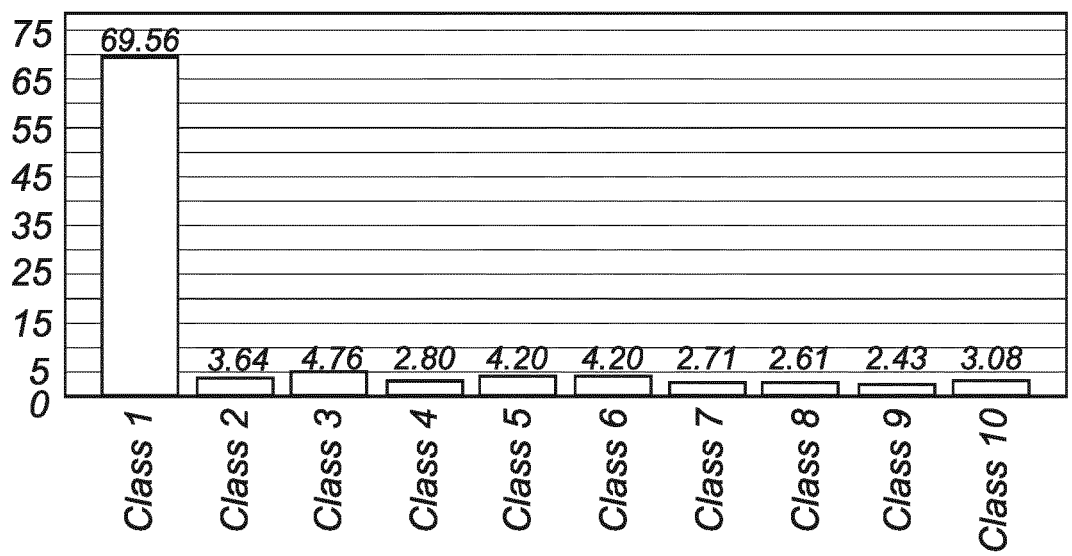
FIG. 3 is a histogram representing a cell size analysis of the hydrophilic polyurethane foam produced according to Example 1.
Figure 4:
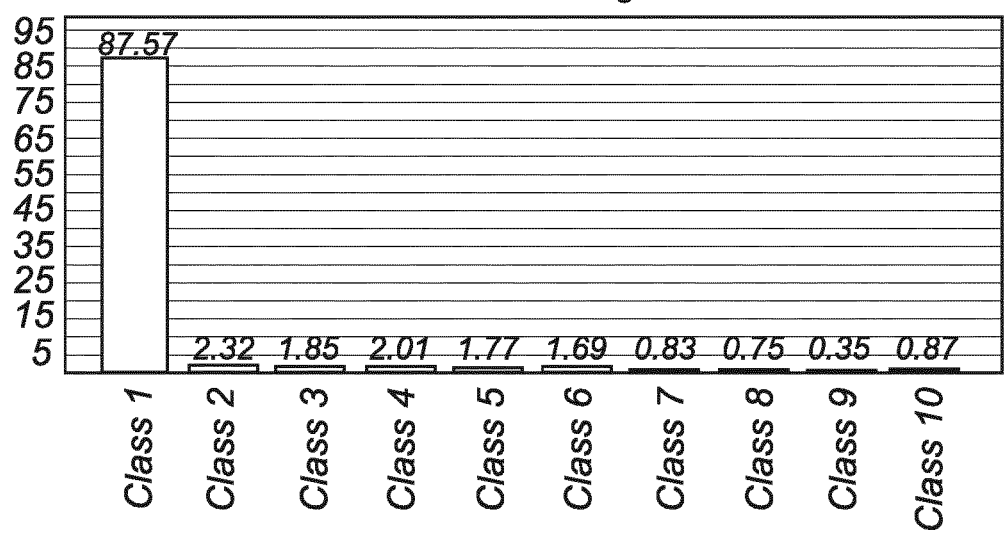
FIG. 4 is a histogram of cell size analysis of the hydrophilic polyurethane foam produced according to Example 2.

Images of cross-sections of the foam layers produced in Example 1 and Example 2 were analyzed according ISO 13322-1 using an Olympus SZX16 microscope and Olympus Stream Image Analysis Software Version 510 (software is based on ISO 13322-1) from Olympus Soft Imaging Solution GmbH, Johann-Krane-Weg 39, D48149 Munster, Germany. FIG. 3 and FIG. 4 are histograms of cell size analysis of the foam material according to Example 1 (without nucleating particles) and Example 2 (with ca. 10% nucleating particles (alumina trihydrate) by weight of the foam material), respectively.

As can be seen in FIG. 4, 87.6% of all foam cells of the hydrophilic polyurethane foam prepared according to Example 2, which foam includes nucleating particles according to an embodiment of the invention, have an average cell size in class 1 (corresponding to 0.01 mm$^2$ or less). In contrast, as can be seen in FIG. 3, 69.6% of all foam cells in the corresponding foam material without added nucleating particles (Example 1) have an average cell size in class 1 (corresponding to 0.01 mm$^2$ or less).

In FIG. 3 and FIG. 4, the classes 1 to 10 correspond to the following average cell sizes: class 1: 0-0.01 mm$^2$, class 2: 0.01-0.02 mm$^2$, class 3: 0.02-0.03 mm$^2$, class 4: 0.03-0.04 mm$^2$, class 5: 0.04-0.05 mm$^2$, class 6: 0.05-0.06 mm$^2$, class 7: 0.06-0.07 mm$^2$, class 8: 0.07-0.08 mm$^2$, class 9: 0.08-0.09 mm$^2$, class 10: 0.09-0.3 mm$^2$.

EXAMPLE 4

Determination of Free Swell Absorptive (Fluid Absorption) Capacity

The free swell absorptive (or maximum absorption) capacity was determined according to EN 13726-1:2002 with the following minor modifications: a test piece with the size 10×10 cm (thickness ca. 3 mm) was used and the free swell absorptive capacity per volume unit of test piece was calculated, i.e. mass (kg) of retained Solution A per volume (m$^3$). Weight per volume provides a more relevant measure (as compared with e.g. weight by weight as suggested in EN 13726-1:2002) when comparing hydrophilic foams with different densities, in particular as the nucleating particles typically increase the foam density. The "weight per volume" values can readily be converted to "weight per weight" by dividing the weight per volume value with the respective density value of the sample. The free swell absorptive capacity values of the foam material of Example 1 and 2 are presented in Table 1 below.

EXAMPLE 5

Determination of speed of absorption

In accordance with the invention, speed of absorption is determined according to TAPPI standard T558 OM-97 (which method inter alia evaluates the absorptive properties of a surface, as the remaining liquid volume on top of the specimen surface is measured as a function of time), wherein the test solution used herein is the Solution A from EN 13726-1, and droplet volume is 30 µl. The speed of absorption of the foam layers of Example 1 and 2 are presented in Table 1 below. As can be seen in Table 1, the foam material of Example 2 (with alumina trihydrate) has approximately 50% greater speed of absorption compared to the foam material of Example 1 (without alumina trihydrate).

TABLE 1

| Test sample | Density (g/cm³) | Speed of absorption (µl/sec.) | Free-swell absorptive capacity (kg/m³ foam) |
|---|---|---|---|
| Foam Example 1 | 0.0947 | 8.1 | 975 |
| Foam Example 2 | 0.1028 | 12.3 | 985 |

The invention claimed is:

1. A hydrophilic polyurethane foam material comprising alumina trihydrate nucleating particles, which are present at a concentration of from 5% to 25% by weight of said foam material, relative to the overall weight of the foam material, wherein at least 85% of all foam cells in said foam material have an average cross-sectional cell size of 0.01 mm2 or less, as measured by image analysis based on ISO 13322-1:2014, wherein said foam material has a free swell absorptive capacity, as measured according to EN 13726-1:2002, of at least 800 kg/m³.

2. The hydrophilic polyurethane foam material according to claim 1, wherein said nucleating particles have a median particle size distribution in the range of from 1 to 30 µm.

3. The hydrophilic polyurethane foam material according to claim 1, wherein at least 99% said nucleating particles are encapsulated within said foam material.

4. The hydrophilic polyurethane foam material according to claim 1, wherein said foam material further comprises a surfactant present at a concentration of from 0.05 to 0.5% by weight, relative to the overall weight of the foam material.

5. The hydrophilic polyurethane foam material according to claim 1, wherein said foam material has a speed of absorption of at least 5 µL/sec, as measured according to TAPPI standard T558 OM-97, using 30 µL Solution A, according to EN 13726-1:2002, as test solution.

6. The hydrophilic polyurethane foam material according to claim 1, wherein said hydrophilic polyurethane foam material is partially obtained from a prepolymer comprising or being an isocyanate-capped polyol or isocyanate-capped polyurethane.

7. The hydrophilic polyurethane foam material according to claim 6, wherein said polyol is selected from the group consisting of a polyester polyol, polyacrylate polyol, polyurethane polyol, polycarbonate polyol, polyether polyol, polyester-polyacrylate polyol, polyurethane polyacrylate polyol, polyurethane polyester polyol, polyurethane polyether polyol, polyurethane polycarbonate polyol, and polyester polycarbonate polyol.

8. The hydrophilic polyurethane foam material according to claim 6, wherein said prepolymer derives from a reaction between a polyol, and a diisocyanate compound selected from the group consisting of hexamethylene diisocyanate (HDI), toluene diisocyanate (TDI), methylene diphenyl diisocyanate (MDI), isophorone diisocyanate (IPDI), and any mixture thereof.

9. A medical dressing comprising a layer of the hydrophilic polyurethane foam material according to claim 1.

10. The medical dressing according to claim 9, wherein said medical dressing further comprises at least one further layer.

11. A method for producing the hydrophilic polyurethane foam material accordingly to claim 1, comprising the steps of:
(i) preparing an aqueous mixture,
(ii) mixing said aqueous mixture with a prepolymer composition, and
(iii) allowing the resulting emulsion to cure wherein alumina trihydrate nucleating particles, at a concentration of from 5% to 25% by weight of said prepolymer composition, are added to said aqueous mixture in step (i) and/or are present in said prepolymer composition of step (ii).

* * * * *